United States Patent
Schenkl (10) Patent No.: US 6,833,555 B2
(45) Date of Patent: Dec. 21, 2004

(54) TURBIDITY SENSOR HAVING ADAPTED TRANSMISSION CHARACTERISTIC AND METHOD FOR FABRICATION THEREOF

(75) Inventor: Johann Schenkl, Bodenwohr (DE)

(73) Assignee: Elektromanufaktur Zangenstein Hanauer GmbH & Co. KGaA, Nabbury (DE)

( * ) Notice: Subject to any disclaimer, the term of this patent is extended or adjusted under 35 U.S.C. 154(b) by 65 days.

(21) Appl. No.: 10/366,098

(22) Filed: Feb. 13, 2003

(65) Prior Publication Data

US 2003/0173530 A1 Sep. 18, 2003

(30) Foreign Application Priority Data

Feb. 14, 2002 (EP) .............................................. 02003147

(51) Int. Cl.[7] .................. G01N 15/06; G01N 21/49; G01N 21/85
(52) U.S. Cl. .................. 250/573; 250/226; 250/574; 73/335.01; 356/436
(58) Field of Search .................. 250/226, 573–574; 356/436; 73/335.01

(56) References Cited

U.S. PATENT DOCUMENTS

| 3,449,578 A |   | 6/1969 | Keim |
|---|---|---|---|
| 4,155,653 A | * | 5/1979 | San Miguel et al. ........ 356/438 |
| 4,257,708 A |   | 3/1981 | Fukuda |
| 4,876,069 A | * | 10/1989 | Jochimsen .................. 422/73 |

* cited by examiner

Primary Examiner—Stephone B. Allen
Assistant Examiner—Patrick J. Lee
(74) Attorney, Agent, or Firm—Wood, Herron & Evans LLP (57) ABSTRACT

For adjusting output voltages of a turbidity sensor which is used for measuring the turbidity of a medium by means of a radiation at least partially propagating through the medium being emitted from a sender and being received by a receiver, ohmic loads for the receiver on its output side are adjusted such that desired output voltages are obtained.

14 Claims, 4 Drawing Sheets

Principle of tolerance variation and shift, respectively

TURBIDITY SENSOR HAVING ADAPTED TRANSMISSION CHARACTERISTIC AND METHOD FOR FABRICATION THEREOF

This application is a continuation of the "parent" European Patent Application Number 02 003 147.2, entitled "Turbidity Sensor Having Adapted Transmission Characteristic And Method For Fabrication Thereof," filed with the European Patent Office on Feb. 14, 2002.

DESCRIPTION

1. Field of the Invention

In general, the present invention relates to turbidity sensors for household appliances, such as dishwashers, washing machines and dryers. In particular, the present invention relates to turbidity sensors wherein the transmission characteristics of single components, for example of a sender and a receiver for optical radiation, are or will be, respectively, matched with respect to each other.

2. Background of the Invention

In household appliances, such as washing machines, dish washers and dryers, it is known to employ turbidity sensors in order to determine the turbidity or dirt level of media used in such household appliances, such as cleaning or washing water and drying air, respectively. For example, it is possible to determine the dirtying of a product to be cleaned on the basis of the turbidity or dirt level of cleaning water or the humidity present in a product to be dried via substances of exhaust air of a dryer or the condition of a fluff sieve of a dryer.

In general, turbidity sensors are comprised of a sender and a receiver for optical radiation that propagates through the used medium. Interactions of the radiation on its propagation path through the medium are used to infer the turbidity or dirt level of the medium.

Turbidity sensors comprises a housing which is arranged in a household appliance such that at least those portions of the housing which comprise the sender and receiver project into the interior of the appliance to direct the radiation through the medium being present at operation of the appliance in its interior.

The transmission characteristic of such turbidity sensors is essential for their operation since it determines accuracy and reliability of turbidity or dirt level detection. For a non damped transmission path between a sender and a receiver of a turbidity sensor, the receiver current generated by the receiver results from a multiplication of the current supplied to the sender for generating the radiation with a constant which is, beside by the parameters given in the following, also affected from those portions of the sensor housing and the medium through which the measuring beam is propagating.

On the sender side, the constant depends from the efficiency of the sender for example the efficiency of a sender diode for optical radiation and the quality of a sender chip used therewith, respectively. Accordingly, on the receiver side, the constant is influenced by the efficiency of the receiver, for example by the quality of a used receiver chip.

To optimize the transmission characteristic of turbidity sensors, i.e. to obtain an output voltage as large as possible or an output current as large as possible on the receiver side for a given voltage or a given current for operation of the sender, usually selected components are used for design of the sender and the receiver. Here, it is known to measure a sender and a receiver and their components, respectively, before design of a turbidity sensor as regards their sending and receiving characteristics, respectively, and, then, to group them accordingly, i.e. to employ senders and receivers matching each other in pairs in turbidity sensors. Due to the required testing of the senders and receivers, this procedure is time consuming and costly and results that, in general, only specific groups of sender and receiver pairings can be used. As an alternative, it is known to supply the sender of a turbidity sensor with power being adjustable over a large range in order to obtain, on the receiver side, signals of desired or required magnitude and quality. This requires a power adjustment on the sender side in dependence of output signals when designing a turbidity sensor. For power adjustment, required components are arranged within the turbidity sensor but are necessary only when designing the turbidity sensor but not for its operation. Beside the required power adjustment in the power supply of the sender, this approach has the drawback that such turbidity sensors comprise components that are not necessary for their actual operation. As an alternative, components required for such a power adjustment are arranged in a unit used for controlling the sensor. In both cases, the sensor is generally operated only at one operating point which is why the components used for power adjustment are not required for actual operation.

Increasingly, such measures are required since the components used in turbidity sensors, in particular senders and receivers, are fabricated with increasingly higher efficiencies and sensitivities (qualities), respectively. In turn, this makes it increasingly difficult to obtain sender-receiver-pairings that exhibit characteristic parameters given for an operation of a household appliance. In other words, the single components for design of a turbidity sensor are increasingly better which is why turbidity sensors exhibit worse measuring characteristics if the sender-receiver-pairings selected for design are not optimally matched with respect to each other.

OBJECT OF THE INVENTION

In general, object of the present invention is to overcome the above named problems of prior art. In particular, the present invention should provide a method for fabrication of turbidity sensors which makes it possible to, on the one hand, use very high quality senders and receivers to compensate their higher absolute values in a simple manner and, on the other hand, to allow for the application of senders and receivers being more imprecise or being selected improperly matched with respect to each other ("non-fitting sender/receiver"). Furthermore, the present invention should provide turbidity sensors having transmission characteristics which compensate the deviation of high quality senders and receivers and which compensate the effects resulting from a combination of imprecise senders and imprecise receivers.

SHORT DESCRIPTION OF THE INVENTION

For a solution of the above object, the present invention provides an apparatus for adjusting of output voltages of a turbidity sensor and accordingly constructed turbidity sensors.

In particular, the present invention provides a method for adjusting (e.g. shifting and/or limiting) of output voltages of a turbidity sensor that serve for determination of the turbidity of a medium by means of radiation, at least partially propagating through the medium, which is emitted from a sender and received from a receiver. For characterizing desired output voltages of the receiver in response to radiation received from the sender of a sender current use for operation of the sender, a desired characteristic curve or a desired characteristic curve range is defined. By means of the real components of the turbidity sensor and in particular of the sender and the receiver, a current characteristic curve is determined which indicates the actual dependency of output voltages of the receiver from sender currents. Based on a comparison of the current characteristic curve with the desired characteristic curve or with the desired characteristic curve range, it is determined whether the output voltages of the receiver correspond with the desired output voltages. If this is not the case, the ohmic load of the receiver on its output side is adjusted such that the desired output voltages are obtained.

Preferably, an integrally formed resistance of the turbidity sensor is adjusted, i.e. varied in its magnitude, such that the desired output voltages are obtained. Herewith is contemplated to employ potentiometers or laser trimmed resistances. Further, for adjusting the ohmic load of the receiver on its output side it is possible to determine the transmission characteristic for the radiation (e.g. wave length dependent) and to determine, in dependence therefrom, resistance values which result in the desired output voltages. Preferable, these measurements are performed for a given or known condition of the medium, for example for an unclouded medium or for a medium having a known dirt level.

Further, the present invention provides a method for adjusting output voltages of a turbidity sensor that determines the turbidity of a medium by means of two radiations having different wavelengths. In dependence of the wavelength the receiver of the turbidity sensor receives, its ohmic load on its output side is adjusted such that, irrespective of the wavelength of the received radiation, essentially the same output voltages result.

Further, the present invention provides turbidity sensors having ohmic loads on its output side adjusted according to the previously mentioned methods.

SHORT DESCRIPTION OF THE FIGURES

In the following description of preferred embodiments, it is referred to the accompanying figures which show.

DESCRIPTION OF PREFERRED EMBODIMENTS

Figure 1:
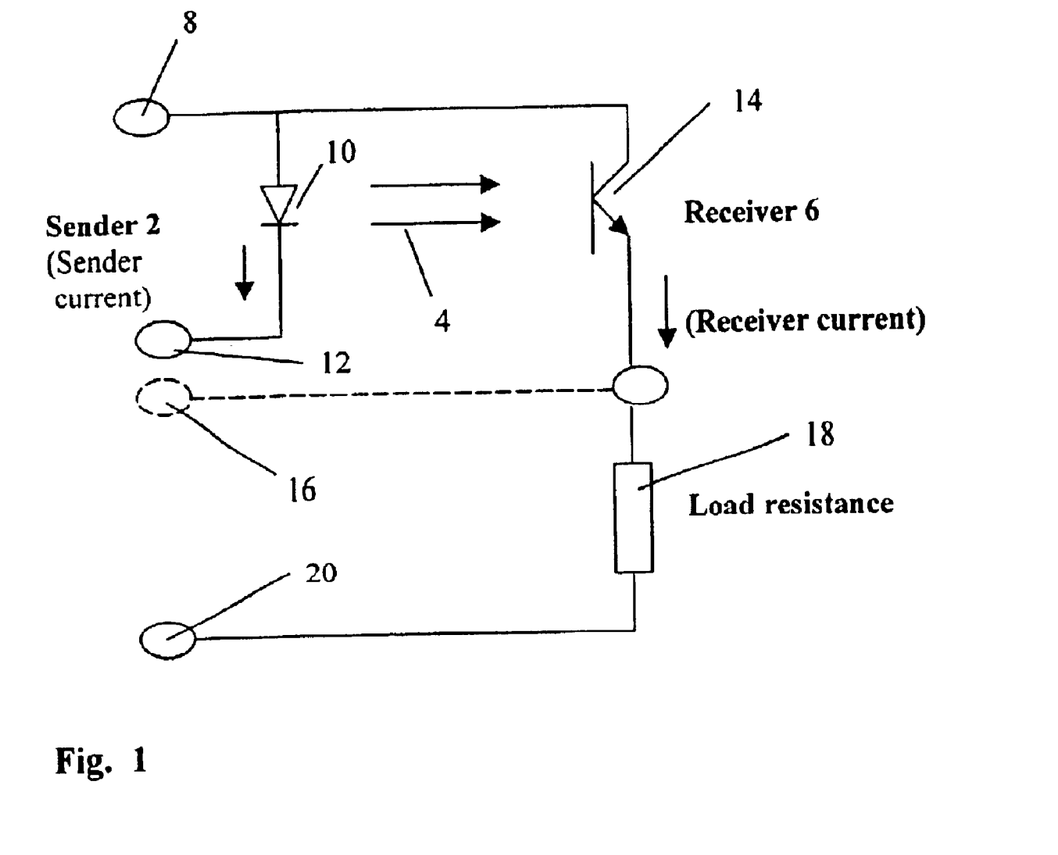
FIG. 1 a schematic illustration of a turbidity sensor having a sender and a receiver, FIG. 2 a schematic illustration of the influence of load resistances for the receiver on output voltages of the turbidity sensor of FIG. 1 in relation to sender currents for the sender of FIG. 1, FIG. 3 characteristic curves for the turbidity sensor of FIG. 1 according to a first output ohmic load on the output side, FIG. 4 characteristic curves for the turbidity sensor of FIG. 1 according to a second ohmic load on the output side, FIG. 5 characteristic curves for the turbidity sensor of FIG. 1 having adapted output ohmic loads on the output side, and FIG. 6 a schematic illustration of a turbidity sensor having two senders and one receiver.

As schematically illustrated in FIG. 1, a turbidity sensor (not indicated) comprises a sender 2, which emits an optical beam 4. The optical beam 4 is received by a receiver 6 that generates a receiver current in dependence of the received radiation intensity. In view of the relation of the radiation intensity emitted by the sender 2 to the radiation intensity received by the receiver 6, interactions of the beam 4 on its propagation path from the sender 2 to the receiver 6, for example through a cleaning or drying medium of a household appliance, are sensed in order to determine the turbidity or dirt level of the medium.

The sender 2 comprises, connected to a potential 8, a sender diode 10 which is connected, on its output side, with a sender potential 12. The potential difference between the potential 8 and the sender potential 12 as well as the properties of the sender diode 10 determine the sender current and, thus, the radiation 4 generated by the sender diode 10. The receiver 6 comprises a receiver transistor 14 that is also connected with the potential 8. So far, the circuitry corresponds with conventional circuitries of senders and receivers of turbidity sensors.

Conventionally, the receiver transistor 14 is, on its output side, connected with a receiver potential 16 that is defined, as the sender potential 12, by means of control electronics (not illustrated). That is, the sender diode 10 and the receiver transistor 14 are respectively connected with corresponding ports of a control electronics. This arrangement is indicated by means of the dotted lines in FIG. 1.

In contrast thereto, in the present invention, the receiver 6, in particular its receiver transistor 14 are, on the output side, connected with a, preferably integrally formed load resistance 18 which, in turn, is connected with a receiver potential 20.

Usually, the potential 8 is connected with a positive supply voltage whereas the sender potential 12 and the receiver potential 15 are connected with the controller and the potential 20 is connected with a reference potential of 0 volt. The potentials 12 and 16 are inputs and control lines, respectively, and the potential 20 serves as reference potential for a controller used for operation of the turbidity sensor wherein a supply potential of the controller is employed as ground for the turbidity sensor.

The radiation power generated by the sender diode 10 is directly proportional to the sender current flowing through the sender diode 10 as long as the sender diode 10 is operated in its linear range. This proportional relation is not prevailing if the sender diode 10 is operated outside its linear range, i.e. if the sender current is small. Accordingly, for operation of the sender diode 10, a sender current has to be used which ensures an operation of the sender diode 10 in its linear range.

In comparable manner this applies to the receiver current generated by the receiver transistor 14. Therefore, the radiation intensity of the beam received by the receiver 6 should be large to such an extent that the receiver transistor 14 is operated in its linear range in order to obtain a proportionality between the received radiation intensity and the generate receiver current.

Since the relative transmission losses of the beam 4 on its propagation path from the sender 2 to the receiver 6 via the housing (not illustrated) of the turbidity sensor are independent from the transmitted radiation power, the following equation is valid for the relation of the receiver current to the sender current:

$$I_e = K \times I_s,$$

wherein $I_e$ indicates the receiver current, K indicates the transmission constant mentioned at the beginning and $I_s$ indicates the sender current.

In line therewith, for an output voltage on the receiver side, essentially dropping off across the load resistance 18, between the potential 20 and the receiver potential 16 the following applies:

$$U_e = I_e \times R = R \times K \times I_s,$$

wherein $U_e$ indicates the receiver voltage on the output side and R indicates the magnitude of the load resistance 18.

Thus, the relation of the receiver voltage $U_e$ to the sender current $I_s$ can be defined as follows:

$$U_e \div Is = K \times R.$$

In order to obtain a desired relation of the receiver voltage $U_e$ and the sender current $I_s$ independent from the transmission characteristic which is essentially determined by the sender 2 and the receiver 6, the magnitude R of the load resistance 18 is varied in dependence from the actual transmission characteristic. Thus, higher transmission constant K can be compensated by means of lower load resistances R and vice versa.

If, for example, a sender having a poor efficiency and a insensitive receiver are used, for a given sender current, an output current being small in relation thereto is resulting. In contrast thereto, for the same sender current, an output current being high in relation thereto is generated if a sender having a high efficiency and a sensitive receiver are utilized. In order to obtain essentially same transmission characteristics for these sender and receiver pairings, in the first case, a load resistance 18 having a high ohmic value or even no load resistance 18 is used, whereas, in the second case, a resistance 18 having a low ohmic value is used. In this manner, in spite of different senders and receivers, in particular in spite of senders and receivers being not optimally matched with respect to each other, for all sender and receiver pairings essentially same output voltages are generated.

The load resistance 18 is adjusted in dependence from the width and/or the position of the tolerance range which results from the respective combination of the optical elements, i.e. in particular the sender 2 and the receiver 6 as well as the housing. The load resistance 18 which is arranged in the sensor housing itself and in particular at the receiver 6, for example on a circuit board, can be adjusted in different ways. Further, it is contemplated to utilize single or several balancing resistance, for example, by means of soldering, in order to adapt an already existing load resistance (for example resistances of coupled components, lines, etc.). Further, laser trimmed resistances can be used and/or resistances embodied as potentiometer can be used. The application of resistances, for example embodied as digital potentiometer, is of particular advantage in applications of a turbidity or dirt level sensor with which very exact measurements are to be carried out and, thus, very exact transmission functions are required. Furthermore, the adaptation of the load resistance 18 can be accomplished by destroying equipped components (resistances already connected with the receiver 6) or separating conducting paths and/or clearing and switching, respectively, of resistances.

For presently available components, usually purchased in selection groups, for turbidity sensors, tolerance ranges having a variation range of approximately +/−60% arise. Thus, for non-matched sender and receiver pairings for a desired output voltage of 1 volt, actual output voltages having values between 0.4 and 1.6 volt result. By means of the adaptation and adjustment, respectively, of the load resistance 18 discussed in the following, these variations can be reduced in dependence of the accuracy of the performance of the adaptation process, for example by factor 10.

In the following, the adaptation of the load resistance 18 is described, for the sake of simplicity, in relation to the sender 2 and the receiver 6. However, this adaptation is applicable also with respect to single or several further components of a turbidity sensor.

In an application of senders and receivers, the technical parameters of which determining the transmission property for the beam 4 are not known, sender 2 and receiver 6 are measured to determine a resistance R for the load resistance 18 which provides the desired output voltage $U_e$.

Due to improved fabrication methods, senders and receivers useable in turbidity sensors are of increasingly high quality, i.e. the absolute values of the optical characteristic parameters are increasingly higher. To aggravate the situation, the higher quality components furthermore exhibit approximately the same proportional spread as previous, worse components. Accordingly, the higher quality component yield higher absolute values but exhibit, as regards its tolerance ranges, proportional variations being comparable with worse components. As set forth above, this can result that the receiver 6 provides a high output current $I_e$. In order to avoid that the output voltage $U_e$ exceeds a desired value, in those cases, generally small resistances R are used for the load resistance 18. By such precisely fabricated senders and receivers, i.e. senders of particularly high efficiency and particularly sensitive receivers, the load resistance 18 serves, on the one hand, to match the sender 2 and the receiver 6 with respect to each other and, on the other hand, "to compensate" the better technical properties of these components. In this manner, by means of an adaptation of the load resistance 18 carried out in dependence from the sender 2 and the receiver 6, a desired transmission characteristic is obtained.

A further advantage of the load resistant 18 is that transmission characteristics can be obtained which otherwise would not be possible with available sender and receiver pairings. This applies, for example, that the receiving characteristic of a receiver intended for use in a turbidity sensor hinders the use of a desired sender. By means of a respective selection of the magnitude of the load resistance 18, the contemplated receiver and the desired sender can be employed in a turbidity sensor although, strictly speaking, these do not "fit with respect to each other".

Further, the load resistance 18 makes it possible to realized not available performance and sensitivity selection groups, respectively, of sender and receiver pairings by adjusting the load resistance 18 correspondingly.

Figure 2:
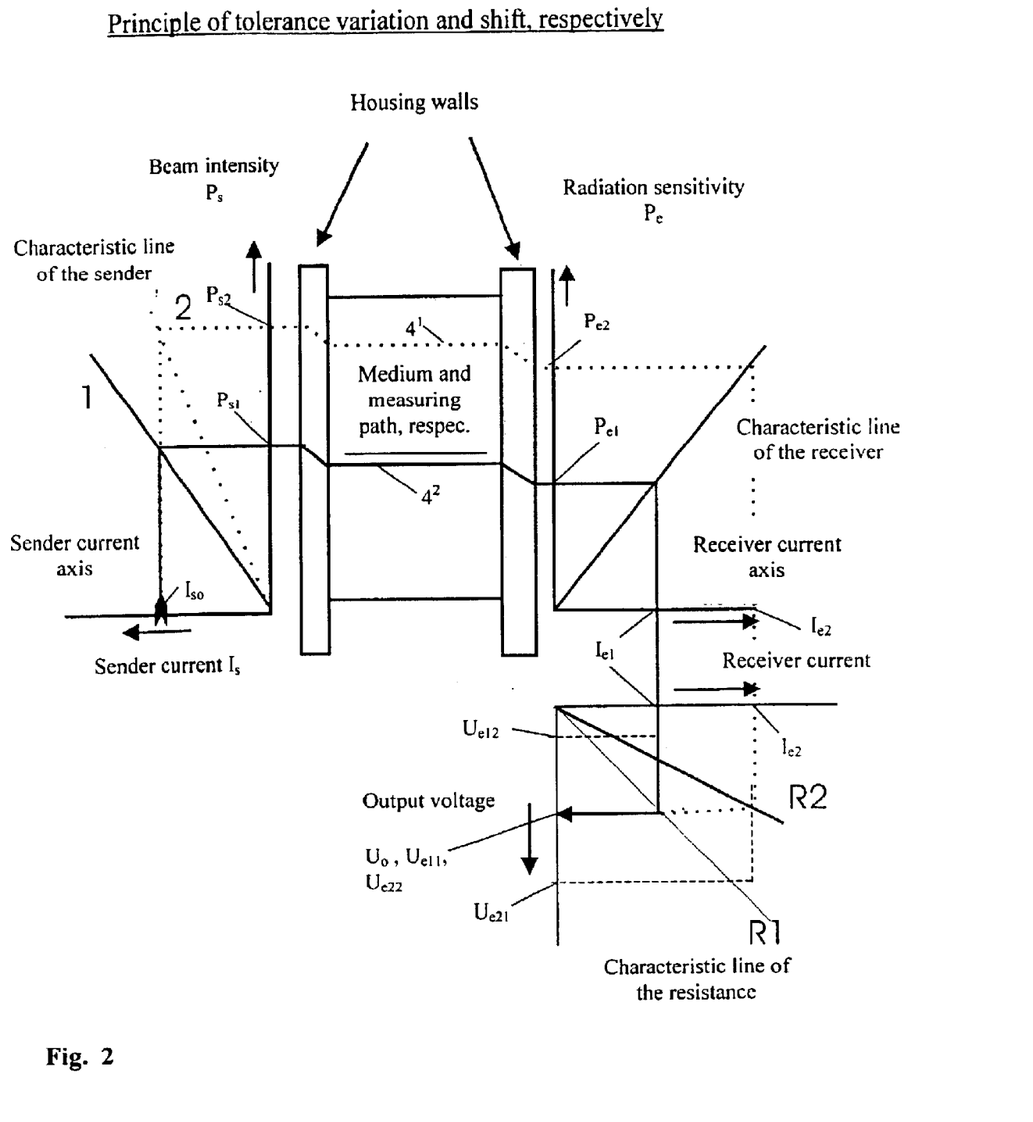

FIG. 2 illustrates the influence of the load resistance 18 on the tolerance range of a turbidity sensor wherein, in the following, the influence of the load resistance 18 is also referred to as tolerance variation and shift, respectively. Left in FIG. 2, the beam intensity $P_s$ of the sender 2 is illustrated in dependence from the sender current $I_s$ wherein sender characteristic lines 1 and 2 indicate senders of different quality (sender characteristic line 1: power sender; sender characteristic line 2: good sender).

Further, right in FIG. 2, the receiver current $I_e$ of the receiver 6 is shown in dependence from the received beam intensity (illumination intensity) $P_e$ for a receiver of a quality.

In addition, housing walls 22 and 24 of the turbidity sensor housing and a portion of a medium 26 to be measured through which the radiation 4 propagates are illustrated.

For a given sender current $I_{s0}$, for the poor sender having the sender characteristic line 1a beam intensity of $P_{s1}$ is resulting, while for the good sender having the sender characteristic line 2 a beam intensity of $P_{s2}$ is resulting.

Therefrom, radiations $4^1$ and $4^2$ are resulting wherein the parallel course of these radiations indicates that they are subjected same interactions on their propagation paths from the sender 2 to the receiver 6.

The receiver 6 receives radiations having a radiation sensitivity $P_{e1}$ for the poor sender and a radiation sensitivity $P_{e2}$ for the good sender. Due to the receiver characteristic line, a receiver current $I_{e1}$ is resulting in response to the radiation acteristic line, a receiver current $I_{e1}$ is resulting in response to the radiation received from the poor sender, while a receiver current $I_{e2}$ results from the radiation originating from the good sender.

Right below in FIG. 2, the output voltage $U_e$ resulting in dependence of the receiver current $I_e$ is shown for a load resistance 18 with the resistance value R2 and for a load resistance 18 with the resistance value R1 being of a higher ohmic value. For the resistance value R2, an output voltage $U_{e12}$ is obtained for the receiver current $I_{e1}$, while the receiver current $I_{e2}$ causes an output voltage $U_{e22}$. For the resistance value R1, output voltages $U_{e11}$ and $U_{e21}$, respectively, are resulting for the receiver currents $I_{e1}$ and $I_{e2}$.

In order to obtain a same output voltage Ue irrespective of the quality of the sender, accordingly, the resistance value R1 is selected for the load resistance 18 for the poor sender (sender characteristic line 1) and for the receiver current $I_{e1}$, respectively, resulting therefrom. In case of the good sender (sender characteristic line 2) and the receiver current $I_{e2}$, respectively, the resistance value R2 is set for the load resistance 18 in order to obtain in both cases the same output voltages, namely $U_{11}$ and $U_{e22}$.

Figure 4:
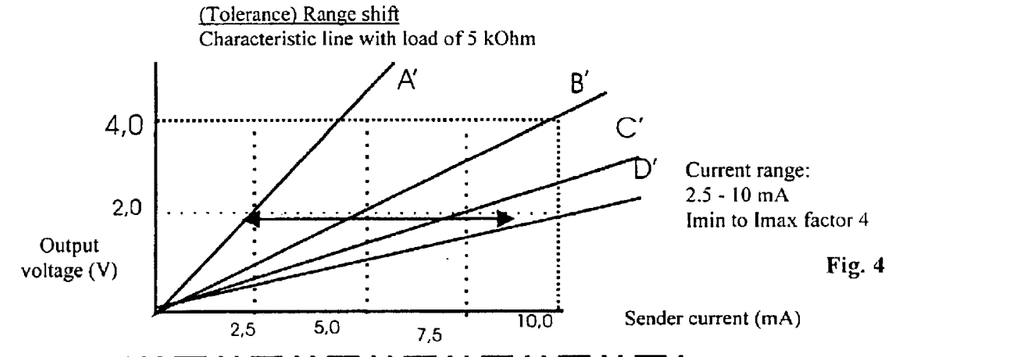
Figure 5:
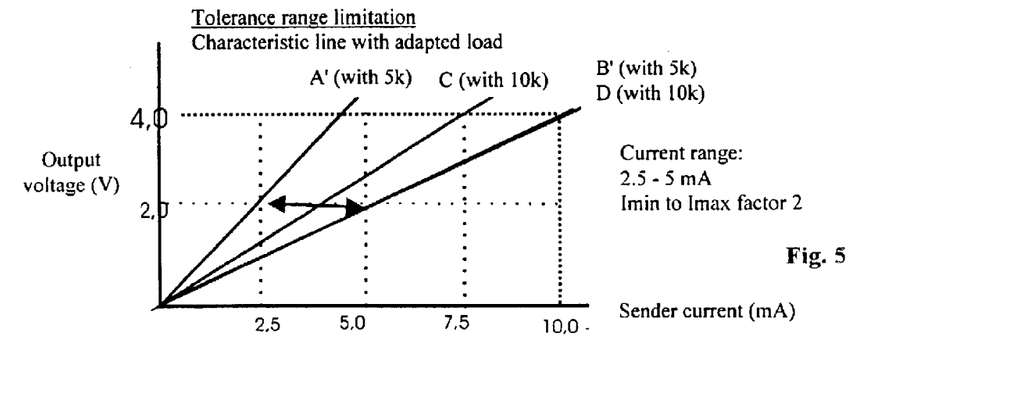

With reference to FIGS. 2, 4 and 5, by means of further characteristic lines for turbidity sensors, the tolerance variation and shift, respectively, via the load resistance 18 is illustrated.

Figure 3:
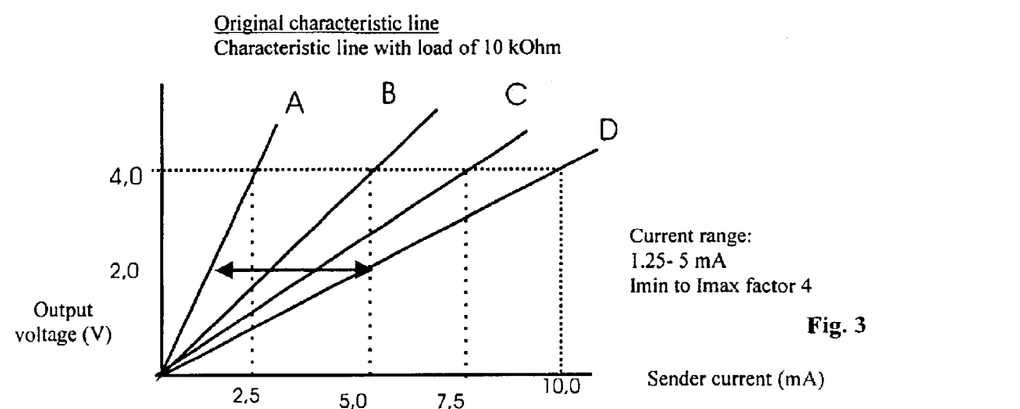

In FIG. 3, the output voltage $U_e$ in dependence of the sender current $I_s$ is illustrated for four characteristic lines A, B, C and D. Here, the characteristic line A represents a good sender-receiver-pairing, while the characteristic lines B, C and D show increasingly poorer of sender-receiver-pairings. Here, it is assumed that the load resistance 18 has a value of 10 kOhm.

Compared with this, FIG. 4 shows a tolerance variation and shift, respectively, for an application of a load resistance 18 having a value of 5 kOhm wherein a characteristic line A' indicates a good sender-receiver-pairing and the characteristic lines B', C' and D' indicate increasingly poorer sender-receiver-pairings.

Starting from the relations between sender currents $I_s$ and output voltages $U_e$ illustrated in FIGS. 3 and 4, for sender-receiver-pairings which exhibits the characteristic lines B/B' and D/D' in dependence of the load resistance 18, essentially the same characteristic lines can be obtained if the load resistance has a value of 5 kOhm for the good sender-receiver-pairing (characteristic line B/B') and has a value of 10 kOhm for the poorer sender-receiver pairing (characteristic line D/D').

Further, by a suitable selection of load resistances 18, a limitation of the range of the output voltages of the receiver 6 can be accomplished by shifting the characteristic lines for sender-receiver-pairings. For example, the range in which the output voltage of the receiver 6 is located, can be limited for the sender-receiver-pairings having the characteristic lines A/A' and C/C' if the load resistance 18 has a value of 5 kOhm for the sender-receiver-pairing having the characteristic lines A/A' and a load resistance 18 having a value of 10 kOhm is selected if for the sender-receiver-pairing having the characteristic lines C/C'.

In addition, by means of using adapted resistance values for the load resistance 18, as indicated by the arrows in FIGS. 3 to 5, the range for the sender current is reduced across which the sender current is varied for different sender-receiver-pairings in order to obtain an output voltage having a given value (for example 2 volt).

Figure 6:
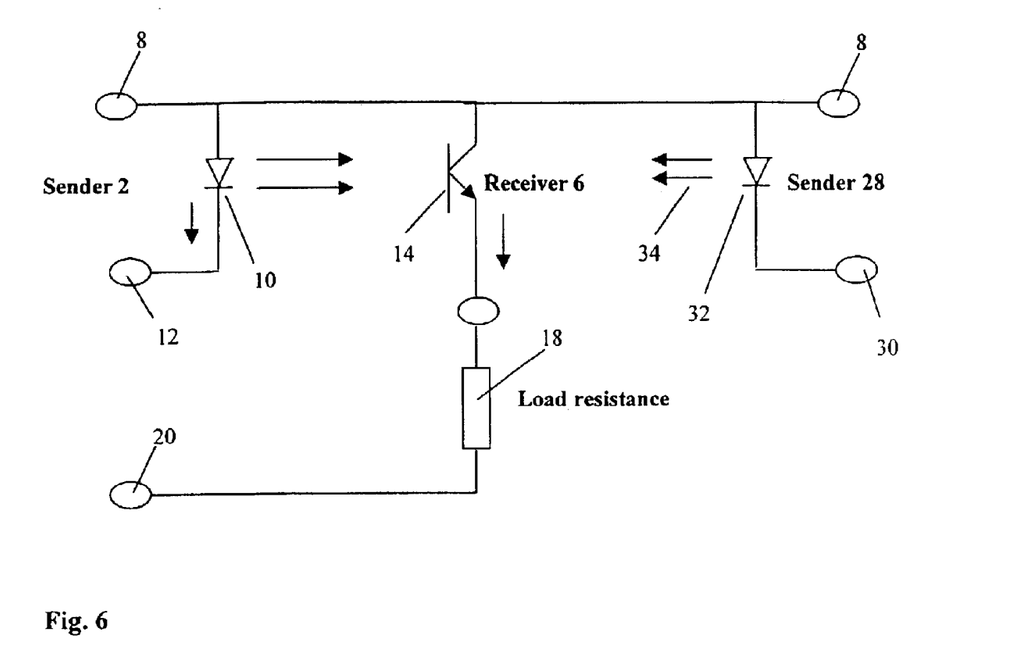

A further application of the above describe adaptation of load resistances and correspondingly constructed turbidity sensors, respectively, are turbidity sensors having two senders which emit radiations of different wavelengths and a receiver which is provided for receipt of both radiations. As illustrated in FIG. 6, such a turbidity sensor is comprised, besides the components illustrated in FIG. 1, by a further sender 28 with a sender diode 32 being connected between the potential 8 and a second sender potential 30. The sender diode 32 emits a radiation 34 the wavelength of which being different from that of the radiation 4. The use of radiations of different wavelength can be employed in order to differentiate a turbidity or dirt level of a medium due to different effects (for example tissue particles, dirt substances, gas bubbles, etc.).

In operation of such a turbidity sensor, the sender 2 and the sender 24 are alternately activated such that the receiver 6 receives the radiations 4 and 34 alternating.

Since the spectral sensitivity of the receiver 6 is given for the receipt of a radiation of a specific wavelength, different output voltages $U_e$ result from a receipt of radiations that exhibit the same intensity but have different wavelengths. If, for example, for the receiver 6, silicon based components having a spectral sensitivity designed for wavelengths in the range of 900 nm, a sender 2 for emission of infrared radiation having a wavelength of approximately 880 nm and a sender 28 for emission of radiation having wavelength of approximately 560 nm (green light) are employed, the sensitivity of the receiver 6 is approximately halved for wavelengths of approximately 560 nm compared with the wave lengths of approximately 880 nm. Accordingly, upon receipt of infrared radiation, an output voltage $U_e$ being approximately doubled results compared with a receipt of a radiation of a wavelength of approximately 560 nm, if both radiations exhibit approximately the same intensity.

In order to obtain, in such cases, approximately the same output voltages $U_e$ irrespective of the wavelength of the radiation 4 and 34, respectively, received from the receiver, the load resistance 18 is varied in dependence of the wavelength of the received radiation.

Here, it is contemplated to determine a first resistance value for the load resistance 18 for adaptation to the sender 2 and a second resistance value for the load resistance 18 for adaptation to the sender 28. In operation of the turbidity sensor schematically illustrated in FIG. 6, the load resistance 18 is adjusted to the first resistance value upon emission and receipt, respectively, of the radiation 4 and to the second resistance value upon emission and receipt, respectively, of the radiation 34. In this manner, approximately equal output voltages $U_e$ are generated independent of the wavelength of the received radiation.

Further, it is contemplated to select the first and second resistance values for the load resistance 18 such that differences in the radiation intensity of the radiations 4 and 5 are also compensated such that in all cases approximately equal output voltages $U_e$ result.

For switching the load resistance 18 between the first and the second resistance values, an electronic circuit, for example integrated into the turbidity sensor, is contemplated, wherein control signals for the senders 2 and 28 can be used as control signals for switching the load resistance 18.

What is claimed is:

1. Method for adjusting output voltages of a turbidity sensor for household appliances for measuring the turbidity of a medium by means of a radiation at least partially propagating through the medium being emitted from a sender and received by a receiver, comprising the following steps:
   defining a desired characteristic line or a desired characteristic line range which characterizes the desired output voltages of the receiver in response to a radiation obtained from the sender in dependence of sender currents for operation of the sender,
   determining a current characteristic line which characterizes the current dependency of output voltages of the receiver from the sender currents,
   comparing the current characteristic line with the desired characteristic line or the desired characteristic line range, and
   varying the ohmic load of the receiver for its output side such that the desired output voltages are obtained if the comparison indicates that the current and the desired characteristic line are different or that the current characteristic line is outside the desired characteristic line range.

2. Method for adjusting output voltages of a turbidity sensor for household appliances for measuring the turbidity of a medium by means of a radiation having a first wavelength, at least partially propagating through the medium, being emitted from a first sender and received by a receiver and by means of a radiation having a second wavelength, at least partially propagating through the medium, being emitted from a second sender and received by the sender, comprising the following steps:
   defining a first desired characteristic line or a first desired characteristic line range which characterizes the desired output voltages of the receiver in response to radiation having the first wavelength obtained from the first sender in dependence of first sender currents for operation of the first sender,
   defining a second desired characteristic line or a second desired characteristic line range which characterizes the desired output voltages of the receiver in response to radiation having the second wavelength received from the second sender in dependence of second sender currents for operation of the second sender,
   determining a first current characteristic line which characterizes the current dependency of first output voltages of the receiver from the first sender currents,
   determining a second current characteristic line, which characterizes the current dependency of second output voltages of the receiver from the second sender currents,
   comparing the first current characteristic line with the first desired characteristic line or the first desired characteristic line range,
   determining a first ohmic load for the receiver for its output side such that the desired output voltages in dependence of the first sender currents are obtained,
   comparing the second current characteristic line with the second desired characteristic line or the second desired characteristic line range,
   determining a second ohmic load for the receiver for its output side such that the desired output voltages in dependence of the second sender currents are obtained, and
   varying the output side ohmic load to the first output side ohmic load if the receiver receives the radiation having the first wavelength and to the second output side ohmic load if the receiver receives the radiation having the second wavelength.

3. Method according to claim 1, wherein for varying the output side ohmic load, a resistance being integrally formed in the turbidity sensor is varied.

4. Method according to claim 1, wherein for varying the output side ohmic load, digital potentiometers or laser trimmed resistances are used.

5. Method according to claim 1, wherein for varying the output side ohmic load
   a current transmission characteristic for the radiation between the sender end the receiver is determined, and
   a resistance value to which the output side ohmic load of the receiver is varied is determined on the basis of the transmission characteristic.

6. A turbidity sensor for household appliances, comprising:
   a sender for emitting a radiation propagating through a medium present in the interior of a household appliance,
   a receiver for receiving radiation generated by the sender wherein a receiver current flowing through the receiver depends on the radiation intensity of the radiation received by the receiver, and
   a load resistance being connected with the receiver on its output side having a resistance value for an ohmic load of the receiver for its output side adjusted according to a method comprising:
      defining a desired characteristic line or a desired characteristic line range which characterizes the desired output voltages of the receiver in response to a radiation obtained from the sender in dependence of sender currents for operation of the sender,
      determining a current characteristic line which characterizes the current dependency of output voltages of the receiver from the sender currents,
      comparing the current characteristic line with the desired characteristic line or the desired characteristic line range, and
      varying the ohmic load of the receiver for its output side such that the desired output voltages are obtained if the comparison indicates that the current and the desired characteristic line are different or that the current characteristic line is outside the desired characteristic line range.

7. Turbidity sensor according to claim 6, wherein the resistance is integrally formed.

8. Turbidity sensor according to claim 6, wherein the resistance is a potentiometer or laser trimmed resistance.

9. A turbidity sensor for household appliances, comprising:
   a first sender for emitting a first radiation having a first wavelength,
   a second sender for emitting a second radiation having a second wavelength,
   a receiver for receiving the first radiation and the second radiation, and
   a load resistance being coupled to the receiver on its output side having first and second resistance values adjusted according to a method comprising:
      defining a first desired characteristic line or a first desired characteristic line range which characterizes the desired output voltages of the receiver in response to radiation having the first wavelength obtained from the first sender in dependence of first sender currents for operation of the first sender, defining a second desired characteristic line or a second desired characteristic line range which characterizes the desired output voltages of the receiver in response to radiation having the second wavelength received from the second sender in dependence of second sender currents for operation of the second sender, determining a first current characteristic line which characterizes the current dependency of first output voltages of the receiver from the first sender currents, determining a second current characteristic line which characterizes the current dependency of second output voltages of the receiver from the second sender currents, comparing the first current characteristic line with the first desired characteristic line or the first desired characteristic line range, determining a first ohmic load for the receiver for its output side such that the desired output voltages in dependence of the first sender currents are obtained, comparing the second current characteristic line with the second desired characteristic line or the second desired characteristic line range, determining a second ohmic load for the receiver for its output side such that the desired output voltages in dependence of the second sender currents are obtained, and varying the output side ohmic load to the first output side ohmic load if the receiver receives the radiation having the first wavelength and to the second output side ohmic load of the receiver receives the radiation having the second wavelength.

10. Turbidity sensor according to claim 9, comprising a control means for adjusting the first and second resistance values for the load resistance in dependence of the operation of the first and the second sender.

11. Turbidity sensor according to claim 10, wherein the control means is operated in dependence of control signals for the first sender and/or the second sender.

12. Method according to claim 2, wherein for varying the output side ohmic load, a resistance being integrally formed in the turbidity sensor is varied.

13. Method according to claim 2, wherein for varying the output side ohmic load, digital potentiometers or laser trimmed resistances are used.

14. Method according to claim 2, wherein for varying the output side ohmic load a current transmission characteristic for the radiation between the sender and the receiver is determined, and a resistance value to which the output side ohmic load of the receiver is varied is determined on the basis of the transmission characteristic.

* * * * *